United States Patent [19]
Reid et al.

[11] Patent Number: 5,461,814
[45] Date of Patent: Oct. 31, 1995

[54] SCENT DISPENSER

[76] Inventors: David R. Reid, 561 Commanche Road, Mississauga, Ontario, Canada, L5H 1W3; James Cuddy, 14 McGill Street Box 242, Marmora, Ontario, Canada, K0K 2M0

[21] Appl. No.: 237,213

[22] Filed: May 3, 1994

[51] Int. Cl.⁶ ................................................. A01N 25/00
[52] U.S. Cl. ................................................................ 43/1
[58] Field of Search .......................... 43/1; 239/36, 55, 239/56, 57; 222/92, 105, 175

[56] References Cited

U.S. PATENT DOCUMENTS

| | | | |
|---|---|---|---|
| 4,186,502 | 2/1980 | Foster | 43/1 |
| 4,682,715 | 7/1987 | Reeves | 43/1 |
| 4,735,010 | 4/1988 | Grinarml | 43/1 |
| 5,074,439 | 12/1991 | Wilcox | 43/1 |
| 5,148,949 | 9/1992 | Luca | 43/1 |
| 5,327,667 | 7/1994 | Fore | 43/1 |

*Primary Examiner*—Kurt Rowan

[57] ABSTRACT

The scent dispenser of the present invention has a casing which is attached to the sole of a boot by means of VELCRO. The casing flexes when compressed by the force exerted upon it by the boot upon contact with the ground and returns to its unflexed condition when the boot is raised from the ground. The casing has a cavity for scented liquid and two or more apertures which communicate the cavity with the atmosphere outside the dispenser. When the casing is compressed, scented liquid is expelled from the cavity through the apertures to the atmosphere. When the cavity is not compressed, the liquid is confined within the cavity.

15 Claims, 3 Drawing Sheets

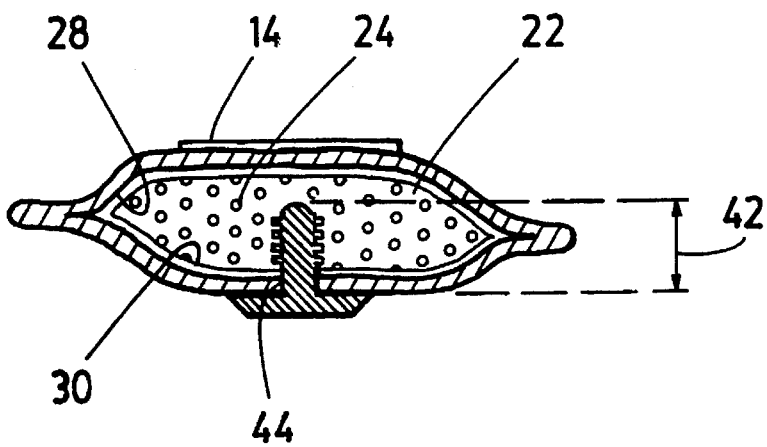
FIG. 4
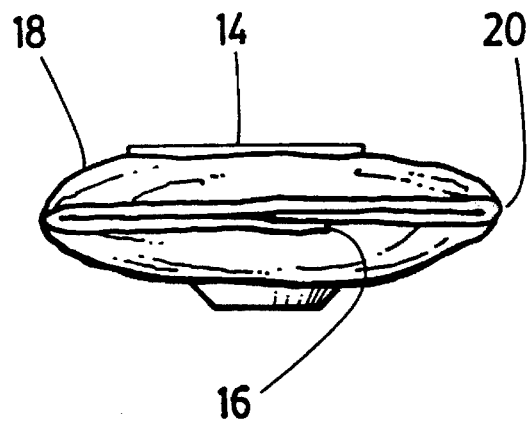
FIG. 5
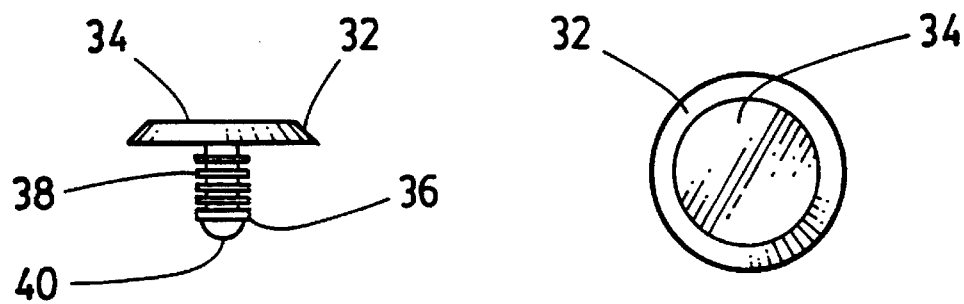
FIG. 6
FIG. 7

SCENT DISPENSER

BACKGROUND OF THE INVENTION

This invention relates to scent dispensers for attracting animals or for concealing the scent of human beings. More particularly the invention relates to a scent dispenser which is removably attached to footwear for releasing a controlled amount of scent each step that the wearer of the footwear takes.

Scented substances which hide human odours from detection by animals are commercially available. Such substances are usually applied in liquid form directly to the boots worn by a hunter or naturalist and are generally quite effective to mask human odour. Such substances have however a number of shortcomings. They have a highly objectionable smell and permanently stain the boots or any clothing in which they come in contact. In addition their effectiveness is generally quite short lived. Once they have evaporated they no longer are very effective in masking human odour.

An additional shortcoming of conventional scents is that their odour lingers on boots. While the odour that lingers is generally not sufficient to mask human scent, it is sufficient to cancel out or interfere with any other scent which is applied later to the same boots. As a result the only scent that may with effectiveness be used on the boots is the one that was originally applied to them. Should the hunter or naturalist wish his boots to give off another scent he will have to wear other boots.

SUMMARY OF THE INVENTION

It is an object of this invention to provide a scent dispenser for scented liquid that discharges a controlled amount of scented liquid each step that the wearer of the footwear takes. The liquid is discharged over a period of time and its effectiveness lasts longer than liquid which is applied directly and all at once to footwear.

Another object of the invention is to provide a scent dispenser which may be attached to footwear for use and afterwards removed from the footwear. The dispenser discharges scent to the atmosphere, to the ground and on the sole of the footwear but not on other areas of the footwear so that staining of those areas by the scented liquid is minimized. In addition where the sole is composed of rubber or other impermeable material, there is little lingering odour on the footwear after the dispenser has been removed.

These and other objects are accomplished by a scent dispenser including: a casing; means for removably attaching the casing to the sole of footwear, the casing flexing when compressed by the force exerted upon it by the footwear upon contact with the ground and returning to its unflexed condition when the compressing force is removed; and a cavity disposed within and surrounded by the casing for receipt of scented liquid, the casing having at least one aperture communicating the cavity with the atmosphere outside the dispenser and being alternately compressed and relaxed upon flexing and unflexing, respectively, of the casing such that scented liquid is expelled from the cavity through the aperture to the atmosphere when the casing is flexed and is substantially confined within the cavity when the casing is unflexed.

DESCRIPTION OF THE DRAWINGS

The scent dispenser of the invention is described with reference to the accompanying drawings in which:

FIG. 4 is a section on line 4—4 of FIG. 1;

FIG. 5 is a view of the side of the dispenser;

FIG. 6 is a side view of a stopper for closing the cavity within the dispenser;

FIG. 7 is a view of the head of the stopper;

Like reference characters refer to like parts throughout the description of the drawings.

DESCRIPTION OF THE PREFERRED EMBODIMENT

Figure 1:
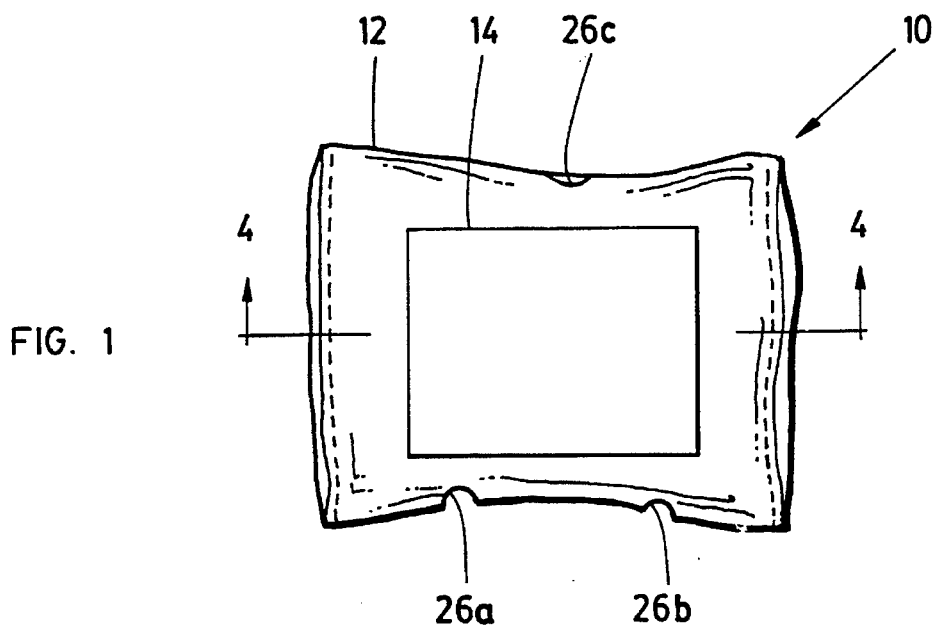
FIG. 1 is a view of the top wall of the scent dispenser.

With reference to FIGS. 1, 4 and 5, the scent dispenser, indicated generally by the numeral 10, includes an outer casing 12 to which is attached a strip of material 14 for attaching the casing to the sole of footwear. The outer casing is composed of a length of material which is folded back upon itself and is attached along an edge 16. Its lateral margins 18, 20 are pinched together and interconnected by gluing and stitching or by other suitable means. The material defines the outer wall of a cavity 22 in which a filler 24 is located.

The filler must be both resilient and liquid absorbent so that it springs back to its original shape after being compressed. The material should preferably be under compression within the cavity so that, being resilient, it will apply outward pressure on the interior walls of the cavity and prevent them from collapsing inward. However, if the material of the casing is itself sufficiently stiff that, in its natural unstressed shape, its upper and lower walls remain separated from one another, as illustrated in FIG. 4, the filler need not be under compression. In such case however, the material of the casing must be resiliently deformable so that it will resume its natural shape when it is not under compression.

Material suitable as a filler include natural or artificial sponges, porous rubber and cellulose.

Apertures 26a,b,c are preferably formed in the front and rear edges of the casing and communicate the cavity with the atmosphere outside the casing. In the preferred embodiment illustrated in the drawings three apertures for permitting the scent to be dispensed are shown. More or less apertures may be used provided the appropriate amount of scent is dispensed over the required area. The interior surface 28 of the casing is preferably coated with a sealant 30 such as uncured polyisobutylene. The sealant may seal the apertures 26 a, b and c and prevent liquid from leaking from the cavity until the apertures are punctured before first use of the dispenser. The sealant may be punctured by means of a needle or a nail. The sealant may eventually reseal the apertures if there are long periods between use of the dispenser and thus prevent leakage during those periods.

Figure 2:
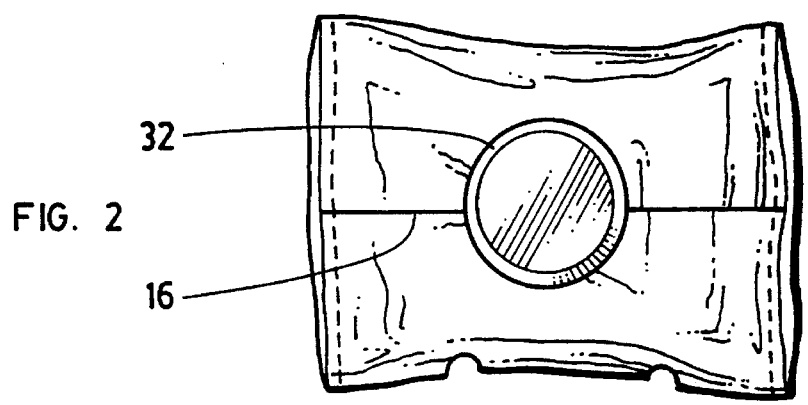
FIG. 2 is a view of the bottom wall of the dispenser.
Figure 3:
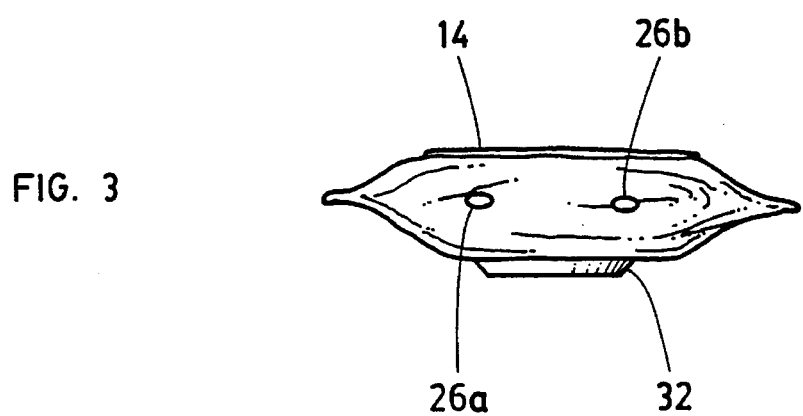
FIG. 3 is a view of the front wall of the dispenser.

With reference to FIGS. 2, 6 and 7, a stopper 32 is inserted into the lower wall of the casing. The stopper has a head 34 and a shank 36. The outer wall of the shank has a plurality of ribs 38 formed thereon and the end of the shank opposite the head is blunted at 40. Preferably the shank is about half as long as the height of the cavity, marked 42 in FIG. 4. The shank will prevent the cavity from fully collapsing when the casing is compressed since its upper end 40 will contact the upper wall of the cavity at this time.

The shank is removably received in an orifice 44 formed in the lower wall of the casing and the head is disposed adjacent to the lower wall. The ribs engage the wall of the casing which defines the orifice and prevent the stopper from accidentally falling out. The only way that the stopper can be removed is for its head to be manually grasped and pulled away from the casing.

When the stopper is removed, the cavity may be filled with scented liquid. Once the stopper is reinserted, it prevents most of the liquid from flowing through the orifice. The filler within the cavity, being absorbent, will maintain the liquid within its interstices when the filler is not compressed so that there will be little leakage of liquid from the cavity at this time. In the preferred embodiment some leakage is desired during use to mask the scent beneath the pad. Only when the filler is compressed will liquid be forced out of it.

The cavity in the dispenser can be filled by injecting scented liquid using a needle-less syringe, or like device, directly into the cavity through apertures 26a, 26b and 26c prior to use. In some cases it may be possible to use a squeezable scent bottle with a nose so long as the nose isn't so big the apertures after being punctured are so large they won't reseal after use. If a syringe is used, on the initial injection of scented liquid into the dispenser cavities, the seal on apertures 26a, 26b and 26c will have to be broken when inserting the syringe. In the preferred embodiment, refilling the syringe and injecting a second amount of scented liquid into the same hole results in the cavity being filled. Once all the cavities are filled, it is advisable to store the dispenser in a self sealing plastic bag until ready for use. To reduce evaporation or leakage of the scented liquid the sealed plastic bag and filled dispensers should be stored in the refrigerator or freezer.

Figure 8:
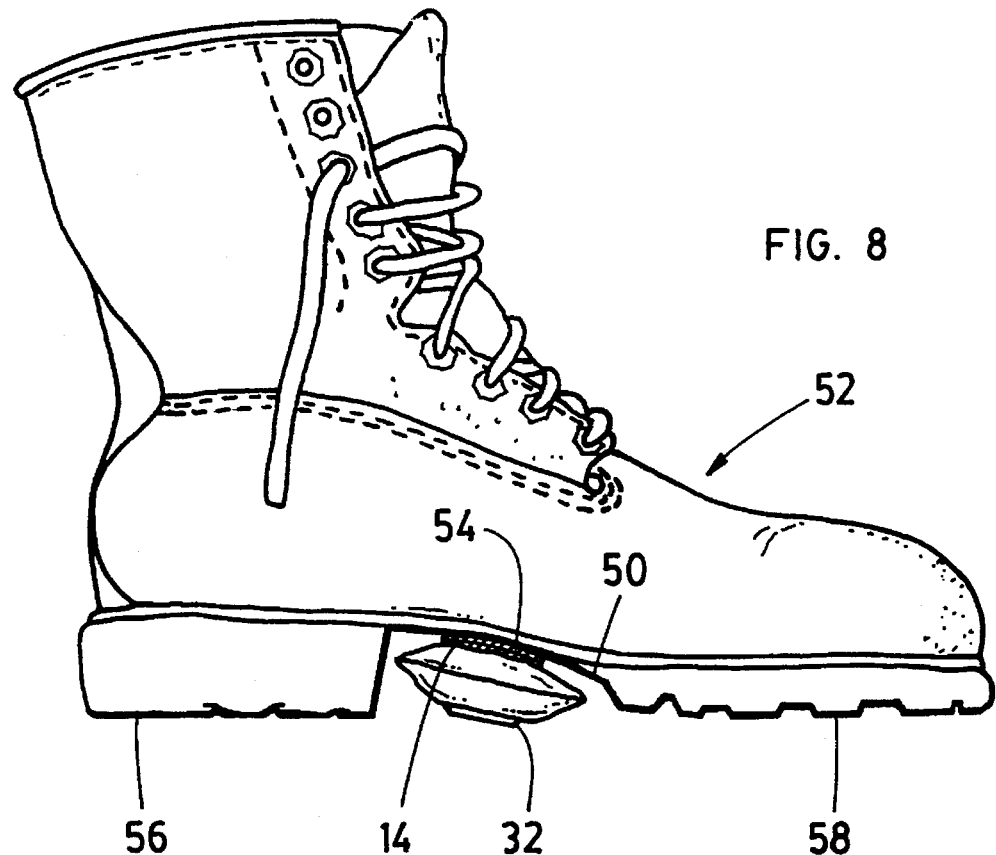
FIGS. 8 and 9 are side and bottom views, respectively, of the dispenser and a boot.
Figure 9:
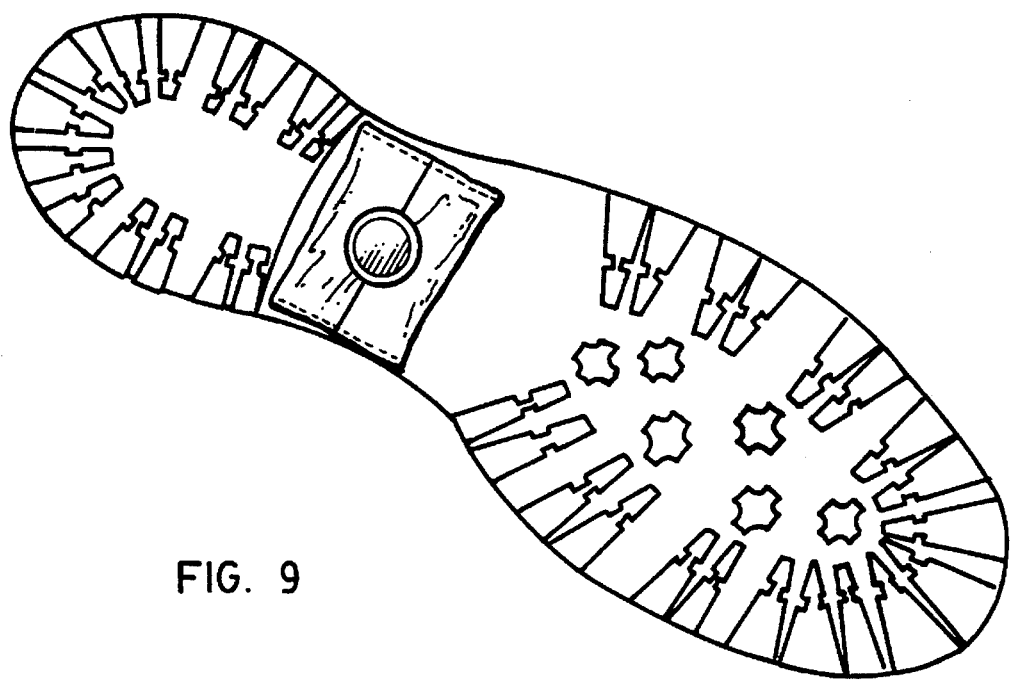

In FIGS. 8 and 9, the dispenser is shown attached to the instep of sole 50 of boot, generally 52. The dispenser is attached by means of a pair of strips 54, 14 of co-operating fasteners constructed of fastening materials which interconnect with one another and which are identified by the trade mark VELCRO. Strip 54 is attached to sole 50 and strip 14 is attached to the upper wall of the dispenser as previously indicated. Preferably strip 54 is protected by a complementary piece of VELCRO when the dispenser is not attached to the boot to prevent dirt, sand and other material from collecting on the strip and impairing its effectiveness.

VELCRO type materials generally include a mass of polymeric hooks on one material and a mass of fibres, strands or loops on an opposite material which receive and hold the hooks. While such materials are preferred for removably attaching the dispenser to a boot, other conventional fasteners could also be used such as buttons, snaps, strings hooks and clasps.

The head 34 of the stopper must extend slightly below the lower walls of the heel 56 and the lowermost area of the sole 58 so that when the boot contacts the ground, the head will likewise contact the ground. The head acts as a skid plate to help protect the lower wall of the casing from abrasion.

Each step that the wearer of the boot takes will cause the dispenser to compress. As the dispenser compresses, scented liquid in the cavity will be forced outward through the apertures. In the preferred embodiment with apertures formed in the front and rear edge of the dispenser the scented liquid is dispensed to the front and rear of the boot to cover the sole of the boot and also to rear to cover the heel of the boot. When the wearer lifts the boot the filler within the casing, or the resilience of the material of the casing, will cause the dispenser to resume its natural shape and liquid still within the cavity will remain there.

The amount of liquid discharged can be varied by increasing or decreasing the number of apertures formed in the dispenser. The amount discharged can also be varied by use of stoppers having differing shank lengths or head thicknesses. If a thicker head is used, the dispenser will extend further below the boot with resulting increased pressure on the dispenser and hence on the scented liquid when the boot contacts the ground. Conversely a thinner head will result in less pressure on the dispenser at this time. Similarly if the shank of the stopper is lengthened, the dispenser will compress less when the boot contacts the ground and less liquid will be discharged.

The casing is composed of tough resilient material such as polyisobutylene which flexes but does not rupture when compressed by the force exerted upon it by the footwear upon contact with the ground. Preferably it is sufficiently resilient that it returns to its unflexed condition when the compressing force is removed. The stopper should be constructed of material which is strong and resists abrasion since its head contacts the ground during each step. Nylon is the preferred material for this purpose.

It will be understood of course that modifications can be made in the preferred embodiment illustrated and described herein without departing from the scope and purview of the invention as defined in the appended claims.

The embodiments of the invention in which an exclusive property or privilege is claimed are defined as follows:

1. A scent dispenser including: a casing; means for removably attaching said casing to the sole of footwear, said casing flexing when compressed by the force exerted upon it by the footwear upon contact with the ground and returning to its unflexed condition when the compressing force is removed; a cavity disposed within and surrounded by said casing for receipt of scented liquid, said casing having at least one aperture communicating said cavity with the atmosphere outside the dispenser and being alternately compressed and relaxed upon flexing and unflexing, respectively, of said casing such that scented liquid is expelled from said cavity through said aperture to the atmosphere when said casing is flexed and is substantially confined within said cavity when said casing is unflexed; a liquid-absorbent filler disposed within said casing; and a stopper removably received in an orifice in said casing, said stopper including an external head for contact with the ground and and internal shank extending into said cavity to engage an interior wall when said casing is compressed to control the compression of said casing.

2. The dispenser as claimed in claim 1 wherein said filler is composed of resilient material under compression within said cavity to cause said casing to return to its unflexed condition when said compression force is removed therefrom.

3. The dispenser as claimed in claim 1 wherein said shank extends approximately half way into said cavity when said casing is in its unflexed condition.

4. The dispenser as claimed in claim 2 wherein said shank extends approximately halfway into such cavity where such casing is in its unflexed condition.

5. The dispenser as claimed in claim 1, wherein said casing is composed of polyisobutylene.

6. The dispenser as claimed in claim 1, wherein said casing is composed of polyisobutylene.

7. The dispenser as claimed in claim 2, wherein said casing is composed of polyisobutylene.

8. The dispenser as claimed in claim 3, wherein said casing is composed of polyisobutylene.

9. The dispenser as claimed in claim 4, wherein said casing is composed of polyisobutylene.

10. The dispenser as claimed in claim 1 wherein said casing is composed of polyisobutylene having on its interior wall a sealant composed of uncured polyisobutylene.

11. The dispenser as claimed in claim 1 wherein there is at least one aperture in the front side of said casing and one aperture in the rear side of said casing.

12. The dispenser as claimed in claim 10 wherein there is at least one aperture in the front side of said casing and one aperture in the rear side of said casing.

13. The dispenser of claim 10 wherein the cavity is filled by injecting the scented liquid into said cavity through the said aperture(s).

14. The dispenser of claim 3 where the cavity is filled by injecting the scented liquid to said cavity through the apertures.

15. The dispenser of claim 1 wherein the head of the stopper, when the casing is flexed and unflexed, acts as a pump to spray the scented liquid through the apertures.

* * * * *